United States Patent
Satou et al.

(10) Patent No.: US 10,550,408 B2
(45) Date of Patent: Feb. 4, 2020

(54) APPARATUS FOR PRODUCING ORGANIC SUBSTANCE AND METHOD FOR PRODUCING ORGANIC SUBSTANCE

(71) Applicant: SEKISUI CHEMICAL CO., LTD., Osaka (JP)

(72) Inventors: Kanetomo Satou, Tsukuba (JP); Kokoro Hamachi, Kawagoe (JP); Yasuyuki Kori, Isesaki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/324,346

(22) PCT Filed: Jul. 27, 2015

(86) PCT No.: PCT/JP2015/071224
§ 371 (c)(1),
(2) Date: Jan. 6, 2017

(87) PCT Pub. No.: WO2016/017572
PCT Pub. Date: Feb. 4, 2016

(65) Prior Publication Data
US 2017/0198309 A1    Jul. 13, 2017

(30) Foreign Application Priority Data

Jul. 30, 2014 (JP) .................................. 2014-154675
Sep. 16, 2014 (JP) .................................. 2014-187448

(51) Int. Cl.
*C12P 1/04* (2006.01)
*C12P 7/08* (2006.01)
(Continued)

(52) U.S. Cl.
CPC .................. *C12P 1/04* (2013.01); *C12M 1/04* (2013.01); *C12M 21/04* (2013.01); *C12M 23/58* (2013.01);
(Continued)

(58) Field of Classification Search
CPC ...... C12M 21/04; C12M 23/58; C12M 43/04; C12P 5/023; C12P 7/08
See application file for complete search history.

(56) References Cited

U.S. PATENT DOCUMENTS

| 5,821,111 A | 10/1998 | Grady et al. |
| 2010/0047886 A1* | 2/2010 | Hickey .................. C12M 21/12  435/140 |

(Continued)

FOREIGN PATENT DOCUMENTS

| JP | 2003-135089 | 5/2003 |
| JP | 2009-136202 | 6/2009 |

(Continued)

OTHER PUBLICATIONS

Phillips et al., "Biological production of ethanol from coal synthesis gas", Springer for Research & Development, vol. 39:Issue 1, pp. 559-571 (1993).

(Continued)

*Primary Examiner* — William H. Beisner
(74) *Attorney, Agent, or Firm* — Wenderoth, Lind & Ponack, L.L.P.

(57) ABSTRACT

The present invention can reduce the amount of carbon dioxide exhausted during the production of an organic substance from waste. The apparatus 1 for producing an organic substance, comprises a synthesis gas generation furnace 11 and a fermenter 13. The synthesis gas generation furnace 11 generates a synthesis gas by partial oxidation of waste. The fermenter 13 contains microorganisms which (Continued)

produce an organic substance from the synthesis gas. The fermenter 13 comprises a first fermenter unit 13a and a second fermenter unit 13b.

7 Claims, 3 Drawing Sheets

(51) Int. Cl.
    *C12M 1/04* (2006.01)
    *C12M 1/107* (2006.01)
    *C12P 5/02* (2006.01)
    *C12M 1/00* (2006.01)
    *C12M 1/34* (2006.01)
    *C12P 7/14* (2006.01)

(52) U.S. Cl.
    CPC ............. *C12M 41/12* (2013.01); *C12P 5/023* (2013.01); *C12P 7/08* (2013.01); *C12M 43/04* (2013.01); *C12P 7/14* (2013.01); *Y02E 50/343* (2013.01)

(56) References Cited

U.S. PATENT DOCUMENTS

| | | | | |
|---|---|---|---|---|
| 2010/0323417 | A1* | 12/2010 | Simpson | C12M 21/12 435/157 |
| 2013/0316411 | A1* | 11/2013 | Schultz | C12M 21/04 435/140 |

FOREIGN PATENT DOCUMENTS

| | | |
|---|---|---|
| WO | 2006/108532 | 10/2006 |
| WO | 2009/058028 | 5/2009 |
| WO | 2010/126382 | 11/2010 |
| WO | 2011/087380 | 7/2011 |
| WO | 2012/026833 | 3/2012 |
| WO | 2013/081779 | 6/2013 |
| WO | 2013/188161 | 12/2013 |
| WO | 2014/077705 | 5/2014 |

OTHER PUBLICATIONS

Partial Supplementary European Search Report dated Feb. 13, 2018 in European Application No. 15828254.1.
International Search Report dated Dec. 22, 2015 in International Application No. PCT/JP2015/071224.
Jamal Abrini et al., "*Clostridium autoethanogenum*, sp. nov., an anaerobic bacterium that produces ethanol from carbon monoxide", Arch Microbiol, vol. 161, No. 4, 1994, pp. 345-351.
K. Thomas Klasson et al., "Bioconversion of synthesis gas into liquid or gaseous fuels", Enzyme Microb., vol. 14, 1992, pp. 602-608.
The First Office Action dated May 9, 2018 in Chinese Patent Application No. 201580037707.2, with English Translation.

* cited by examiner

APPARATUS FOR PRODUCING ORGANIC SUBSTANCE AND METHOD FOR PRODUCING ORGANIC SUBSTANCE

TECHNICAL FIELD

The present invention relates to an apparatus for producing an organic substance and a method for producing an organic substance.

DESCRIPTION OF RELATED ART

In recent years, researches have been made for practical implementation of a method for producing a chemical substance such as ethanol by microbial fermentation of a carbon monoxide-containing synthesis gas aquired from an exhaust gas from a steelworks and the like (see, for example, Patent Document 1).

DOCUMENTS OF RELATED ART

Patent Document

[Patent Document 1] International Patent Application Publication No. 2011/087380

SUMMARY OF THE INVENTION

Problems to be Solved by the Invention

However, heretofore, a practically applicable apparatus for producing an organic substance from waste has not yet been developped, and the fact is that even sufficient research thereon has not been made.

It has been desired to reduce the amount of carbon dioxide exhausted during the production of an organic substance from waste.

It is a primary object of the present invention to reduce the amount of carbon dioxide exhausted during the production of an organic substance.

Means to Solve the Problems

With respect to the apparatus of the present invention for producing an organic substance, the apparatus in a first embodiment thereof comprises a synthesis gas generation furnace and a fermenter. The synthesis gas generation furnace generates a synthesis gas by partial oxidation of the waste. The fermenter contains a microorganism which produces an organic substance from the synthesis gas. The fermenter comprises a first fermenter unit and a second fermenter unit. The first fermenter unit is connected to the synthesis gas generation furnace. The first fermenter unit contains *Clostridium autoethanogenum* as the microorganism. The second fermenter unit is connected to the first fermenter unit. The second fermenter unit contains *Clostridium ljungdahlii* as the microorganism.

With respect to the apparatus of the present invention for producing an organic substance, the apparatus in a first embodiment thereof preferably comprises a methane fermenter for producing methane by subjecting the carbon dioxide generated in the fermenter to methane fermentation. Such an apparatus of the first embodiment of the present invention may further comprise a synthesis gas generation furnace for generating a synthesis gas from methane produced in the methane fermenter.

With respect to the apparatus of the present invention for producing an organic substance, the apparatus in a second embodiment thereof comprises: a fermenter for producing carbon dioxide and an organic substance by microbial fermentation of a synthesis gas; and a methane fermenter for producing methane by subjecting the carbon dioxide generated in the fermenter to methane fermentation.

Tthe apparatus of the second embodiment of the present invention may further comprise a synthesis gas generation furnace for generating a synthesis gas from the methane produced in the methane fermenter.

DETAILED DESCRIPTION OF THE INVENTION

With respect to the method of the present invention for producing an organic substance from waste, the method in a first embodiment thereof comprises: a synthesis gas generation step of generating a synthesis gas by partial oxidation of waste in a synthesis gas generation furnace; a first fermentation step of feeding the synthesis gas to a first fermenter unit containing *Clostridium autoethanogenum* to ferment the synthesis gas; and a second fermentation step of feeding the gas exhausted from the first fermenter unit to a second fermenter unit containing *Clostridium ljungdahli* to ferment the gas.

In the method of the first embodiment of the present invention, it is preferred that the first fermentation step is performed such that the exhaust gas contains hydrogen.

The method of the first embodiment of the present invention preferably further comprises a step of subjecting the carbon dioxide generated in the fermentation step to methane fermentation to thereby obtain methane. Such a method of the first embodiment of the present invention may further comprise a step of generating the synthesis gas from the methane.

With respect to the method of the present invention for producing an organic substance from waste, the method in a second embodiment thereof comprises: a fermentation step of subjecting a synthesis gas to microbial fermentation in a fermenter to obtain carbon dioxide and an organic substance; and a step of subjecting the carbon dioxide generated in the fermentation step to methane fermentation to thereby obtain methane.

In the method of the second embodiment of the present invention, the method may further comprise a step of generating the synthesis gas from the methane.

Effect of the Invention

As described above, the present invention can reduce the amount of carbon dioxide exhausted during the production of an organic substance.

DESCRIPTION OF THE EMBODIMENTS

Hereinbelow, the present invention will be described in detail with reference to preferred embodiments of the present invention. However, these embodiments are only examples. The present invention is in no way limited by these embodiments.

(First Embodiment)

Figure 1:
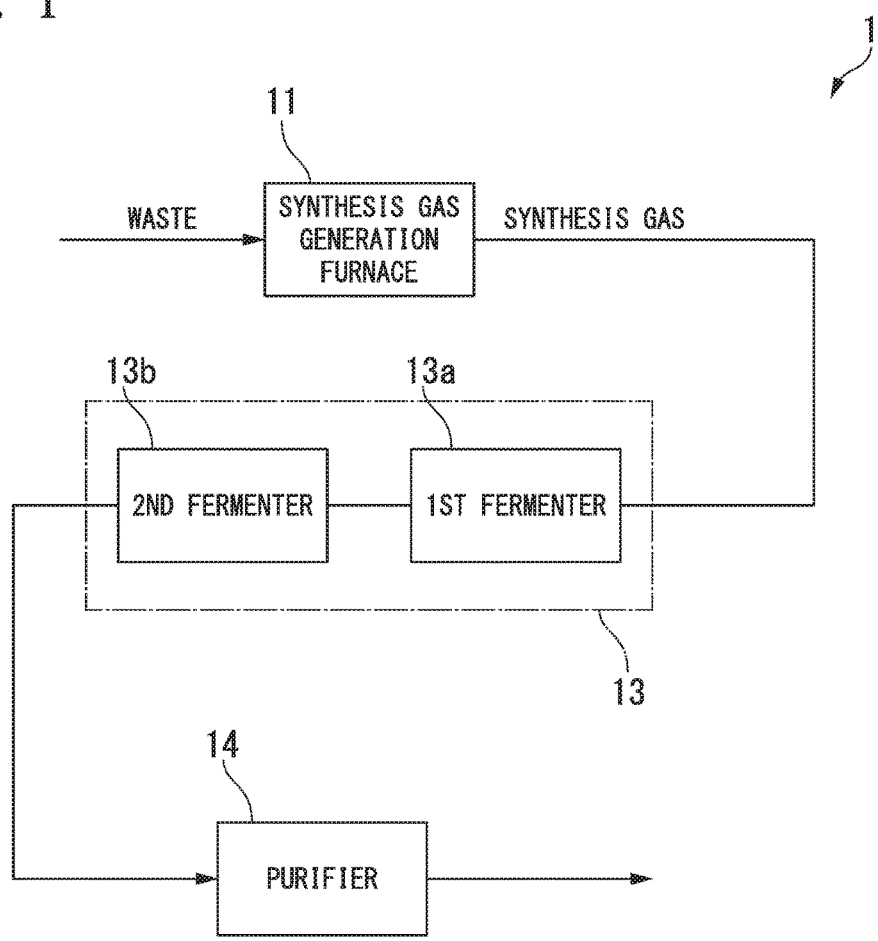
FIG. 1 is a schematic view of the apparatus for producing an organic substance according to a first embodiment of the present invention.

FIG. 1 is a schematic view of the apparatus for producing an organic substance from waste. The apparatus 1 shown in FIG. 1 is an apparatus for producing an organic substance from waste including waste plastic and the like. For example, the organic substance to be produced may be alcohols, organic acids, fatty acids, fats and oils, ketones, biomass, saccharides and the like. More specific examples of the organic substance include ethanol, acetic acid, butanediol and the like.

The obtained organic substance may be used for any purposes without any limitation. For example, the obtained organic substance can be used not only as a material for plastic, resin and the like, but also as fuel.

The apparatus 1 comprises a synthesis gas generation unit 11, a fermenter 13 and a purifier 14. A waste containing organic substances such as plastic, resin and the like is fed into the synthesis gas generation furnace 11. In the synthesis gas generation furnacell, the waste is partially oxidized so as to generate a synthesis gas. Generally, the obtained synthesis gas contains carbon dioxide, hydrogen gas, and nitrogen gas, in addition to carbon monoxide.

The synthesis gas generation furnace 11 is connected to the fermenter 13. The obtained synthesis gas is fed from the synthesis gas generation furnace 11 into the fermenter 13. The fermenter 13 contains microorganisms. The microorganisms produce a target organic substance from the synthesis gas.

The fermenter 13 is connected to the purifier 14. Then, the products in the fermenter 13 (containing the target organinc substance) are transferred to the purifier 14. Generally, the products in the fermenter 13 include another organic substance in addition to the target organinc substance. The purifier 14 purifies the products transferred from the fermenter 13. In such a manner as described above, the target organic substance can be obtained.

The fermenter 13 comprises a first fermenter unit 13a and a second fermenter unit 13b. The first fermenter unit 13a is connected to the synthesis gas generation furnace 11. The first fermenter unit 13a contains *Clostridium autoethanogenum* as the microorganism.

The second fermenter unit 13b is connected to the first fermenter unit 13a. The second fermenter unit 13b contains *Clostridium ljungdahlii* as the microorganism.

The *Clostridium autoethanogenum* contained in the first fermenter unit 13a consumes carbon monoxide and hydrogen so as to produce the organic substance while exhausting carbon dioxide. Therefore, in the case where only the first fermenter unit 13a is provided, the amount of carbon dioxide exhausted from the apparatus 1 is increased.

In the apparatus 1, the waste is partially oxidized in the synthesis gas generation furnace 11 such that the resultant synthesis gas contains carbon monoxide and hydrogen at a molar ratio of approximately 1:1. The *Clostridium autoethanogenum* consumes carbon monoxide more than hydrogen. Therefore, the exhausted gas from the first fermenter unit 13a contains hydrogen together with carbon dioxide. Such an exhausted gas is fed into the second fermenter unit 13b. The second fermenter unit 13b contains *Clostridium ljungdahlii* as the microorganism. In the presence of hydrogen, the *Clostridium ljungdalii* consumes carbon dioxide while producing the organic substance. Therefore, the amount of carbon dioxide exhausted from the apparatus 1 is reduced. In contrast, the amount of organic substances produced in the apparatus 1 is increased.

The present embodiment has been explained above, taking as an example the apparatus 1 comprising the synthesis gas generation furnace 11. However, the present invention is in no way limited to such a configuration. The synthesis gas generation furnace may be provided separately from the apparatus 1 shown in FIG. 1.

Hereinbelow, the present invention will be described in detail with reference to further preferred embodiments of the present invention. In the following descriptions, components having substantially the same functions as those in the first embodiment are denoted with the same reference numerals, and the descriptions thereof are omitted.

(Second Embodiment)

Figure 2:
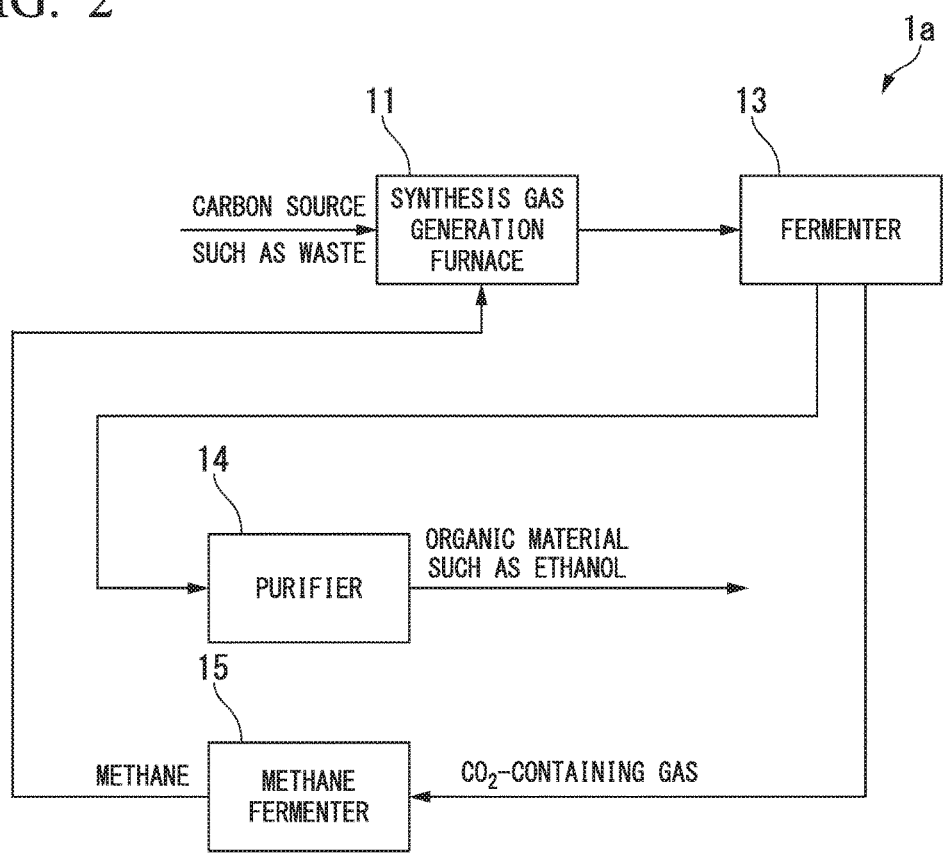
FIG. 2 is a schematic view of the apparatus for producing an organic substance according to a second embodiment of the present invention.

The apparatus 1a shown in FIG. 2 is an apparatus for producing an organic substance by microbial fermentation of a gas obtained by partial oxidation of a carbon source.

For example, the carbon source may be either a waste containing plastic or resin, or a coke and the like.

The organic substance to be produced may be an oxygen-containing organic substance. For example, the organic substance to be produced may be alcohols, organic acids, fatty acids, fats and oils, ketones, biomass, saccharides and the like. More specific examples of the organic substance include ethanol, acetic acid, butanediol and the like.

The obtained organic substance may be used for any purposes without any limitation. For example, the obtained organic substance can be used not only as a material for plastic, resin and the like, but also as fuel.

The apparatus 1a has a synthesis gas generation furnace 11. In the synthesis gas generation furnace 11, a partial oxidation of the carbon source is performed. The partial oxidation of the carbon source in the synthesis gas generation furnace 11 results in generation of a synthesis gas containing carbon monoxide (synthesis gas generation step). Generally, the obtained synthesis gas contains carbon dioxide and hydrogen, in addition to carbon monoxide. The synthesis gas may further contain, for example, a hydrocarbon and the like.

In the case where the carbon source is waste, the synthesis gas generation furnace 11 may be, for example, a waste incinerator. In the case where the carbon source is coke, the synthesis gas generation furnace 11 may be, for example, a steelmaking furnace.

The synthesis gas generation furnace 11 is connected to the fermenter 13. The fermenter 13 contains microorganisms and water. Namely, water containing microorganisms is disposed in the fermenter 13. In the fermenter 13, the microorganisms perform the fermentation of the synthesis gas. As a result, the target organic substance can be obtained. The microorganisms may be anaerobic bacteria. As specific examples of the microorganisms preferably used for producing an alcohol such as ethanol, those belonging to the genus *Clostridium* and the like can be mentioned. In the fermenter 13, in addition to the target organic substance, carbon dioxide is produced.

The fermenter 13 is connected to the purifier 14. A part of the resultant products in the fermenter 13 (containing the target organinc substance) are transferred to the purifier 14. Generally, the products in the fermenter 13 include another organic substance in addition to the target organinc substance. The purifier 14 purifies the products transferred from the fermenter 13 (purification step). In such a manner as described above, the target organic substance can be obtained. In the purifier 14, a residue of the microorganism fermentation is formed together with the target organic substance. Generally, the residue contains organic substances which are not intended to be produced, dead microorganisms, water and the like.

Further, the fermenter 13 is connected to a methane fermenter 15. From the fermenter 13, carbon dioxide and hydrogen are fed into the methane fermenter 15. The carbon dioxide fed to the fermenter 15 contains carbon dioxide contained in the synthesis gas and carbon dioxide formed by microbial fermentation in the fermenter 13. In the methane fermenter 15, the carbon dioxide and the hydrogen, fed from the fermenter 13, are subjected to methane fermentation so as to produce methane. As a result, the amount of carbon dioxide exhausted from the apparatus 1a is reduced. Moreover, methane can be obtained in addition to the target organic substance such as alcohol. In the apparatus 1a, the obtained methane is fed to the synthesis gas generation furnace 11 as a raw material. Therefore, the ratio of the organic substances to be produced to the carbon source to be fed (i.e., amount of the organic substance to be produced/amount of the carbon source to be fed) can be increased. The obtained methane may be recovered and used for other purposes.

In this second embodiment, the methane obtained in the methane fermenter 15 is partially oxidized in the synthesis gas generation furnace 11 to thereby generate a synthesis gas. However, the present invention is in no way limited to the above embodiment. For example, the synthesis gas may be produced by steam reforming of the methane or carbon dioxide reforming of the methane. The methane may also be used as a fuel.

In this second embodiment, the synthesis gas from the first fermenter unit 13a is fed into the second fermenter unit 13b. The water from the first fermenter unit 13a is not necessarily required to be fed into the second fermenter unit 13b. For example, at least a part of the water from the first fermenter unit 13a may not be fed into the second fermenter unit 13b.

(Third Embodiment)

Figure 3:
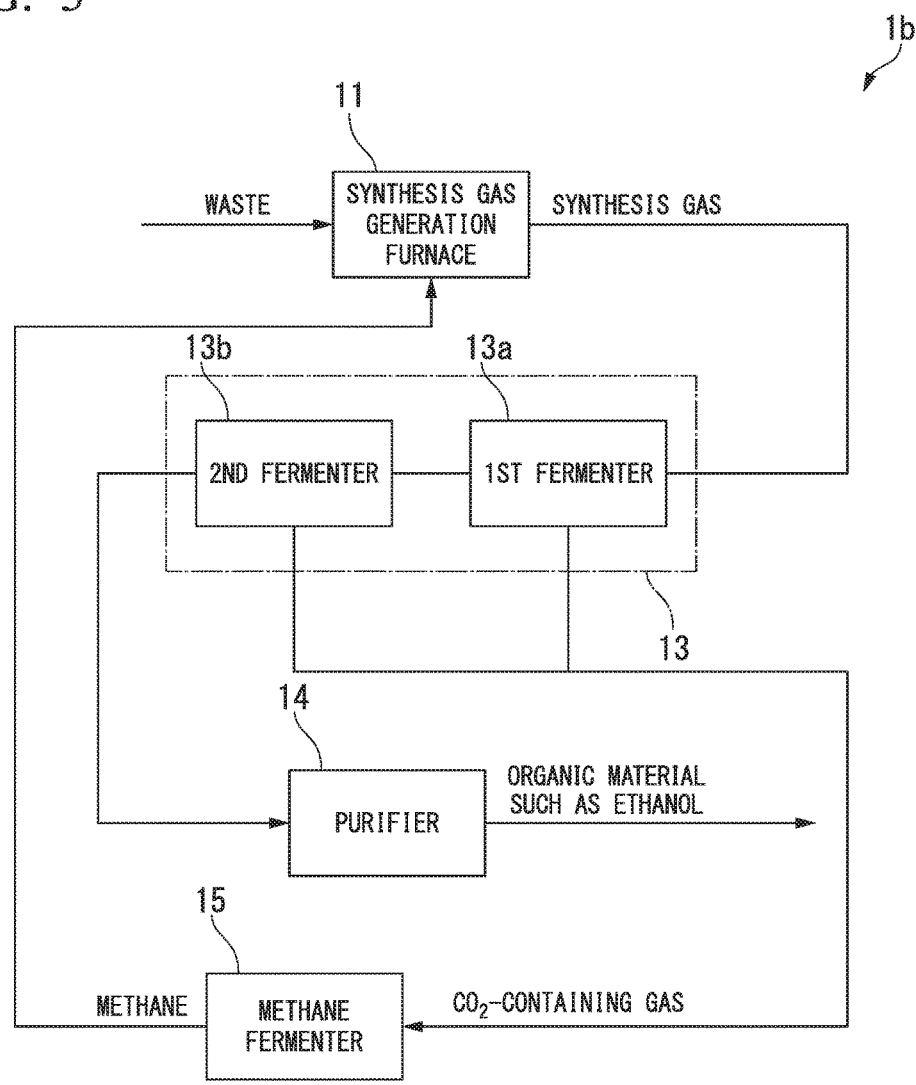
FIG. 3 is a schematic view of the apparatus for producing an organic substance according to a third embodiment of the present invention.

FIG. 3 is a schematic view of the apparatus 1b for producing an organic substance according to the third embodiment.

The apparatus 1b is different from the apparatus 1a of the second embodiment in that the fermenter 13 has the first fermenter unit 13a and the second fermenter unit 13b. The first fermenter unit 13a has substantially the same configuration as the first fermenter 13a of the first embodiment. The second fermenter unit 13b has substantially the same configuration as the second fermenter unit 13b of the first embodiment.

In this third embodiment, the methane fermenter 15 is connected to each of the first fermenter unit 13a and the second fermenter unit 13b. Carbon dioxide generated in at least one of the first fermenter unit 13a and the second fermenter unit 13b is fed into the methane fermenter 15. Carbon dioxide contained in the synthesis gas may be further supplied to the methane fermenter 15. The carbon dioxide fed into the methane fermenter 15 is subjected to methane fermentation so as to generate methane. At least a part of the methane generated in the methane fermenter 15 is fed to the synthesis gas generation furnace 11 and then is partially oxidized so as to become a synthesis gas.

In this third embodiment, as in the first embodiment, the second fermenter unit 13b containing *Clostridium ljungdahlii* is connected downstream of the first fermenter unit 13a containing *Clostridium autoethanogenum*. Therefore, also in this third embodiment, as in the first embodiment, the effect of reducing the amount of carbon dioxide exhausted from the fermenter 13 is achieved.

Further, at least a part of the carbon dioxide generated in the fermenter 13 is subjected to methane fermentation in the methane fermenter 15 so as to obtain methane. As a result, the amount of carbon dioxide exhausted from the apparatus 1b can be further reduced.

Still further, at least a part of the obtained methane is partially oxidized so as to become a synthesis gas. Therefore, the ratio of the organic substances to be produced to the carbon source to be fed (i.e., amount of the organic substance to be produced/amount of the carbon source to be fed) can be increased.

In the first and third embodiments of the present invention, the microorganism cultured in the first fermenter unit 13a and the microorganism cultured in the second fermenter unit 13b are different from each other. Therefore, it is preferable to connect each of the first fermenter unit 13a and the second fermenter unit 13b to a regulator for maintaining the composition of culture solution and the pH within suitable ranges for the fermentation performed in the fermenter unit.

(Fourth Embodiment)

The second and third embodiments have been explained above, taking as an example the case where methane is obtained by methane fermentation of carbon dioxide generated in the fermenter 13. In the present invention, the residue formed in the purifier 14 may be used as a raw material for methane fermentation, in addition to the carbon dioxide generated in the fermenter 13. That is, the residue of the purifier 14 may be fed into the methane fermenter 15 so as to subject the residue to methane fermentation therein. Thus, the amount of methane produced in the methane fermenter 15 can be increased. As a result, for example, in the case where the synthesis gas is produced from methane, the ratio of the organic substances to be produced to the carbon source to be fed (i.e., amount of the organic substance to be produced/amount of the carbon source to be fed) can be further increased.

DESCRIPTION OF THE REFERENCE SIGNS

1, 1a, 1b: Apparatus
11: Synthesis gas generation furnace
3: Fermenter
13a: First fermenter unit
13b: Second fermenter unit
14: Purifier
15: Methane fermenter

What is claimed is:

1. An apparatus for producing an organic substance, comprising:
    a synthesis gas generation furnace for generating a synthesis gas by partial oxidation of waste;
    a fermenter containing microorganisms which produce an organic substance from the synthesis gas, wherein the organic substance is selected from the group consisting of an alcohol, an organic acid, a fatty acid, a fat and oil, a ketone, a biomass and a saccharide; and
    a methane fermenter for producing methane by subjecting carbon dioxide generated in the fermenter to methane fermentation,
    wherein the fermenter comprises:
    a first fermenter unit connected to the synthesis gas generation furnace and containing *Clostridium*

*autoethanogenum* and not containing *Clostridium ljungdahlii* as the microorganism; and a second fermenter unit connected to the first fermenter unit and containing *Clostridium ljungdahlii* and not containing *Clostridium autoethanogenum* as the microorganism.

2. The apparatus according to claim 1, which further comprises a synthesis gas generation furnace for generating a synthesis gas from the methane produced in the methane fermenter.

3. The apparatus according to claim 1, wherein the organic substance is selected from the group consisting of ethanol, acetic acid and butanediol.

4. A method for producing an organic substance, comprising:

a synthesis gas generation step of generating a synthesis gas by partial oxidation of waste in a synthesis gas generation furnace;

a first fermentation step of feeding the synthesis gas to a first fermenter unit containing *Clostridium autoethanogenum* and not containing *Clostridium ljungdahlii* to ferment the synthesis gas, thereby obtaining an organic substance;

a second fermentation step of feeding the gas exhausted from the first fermenter unit to a second fermenter unit containing *Clostridium ljungdahli* and not containing *Clostridium autoethanogenum* to ferment the gas, thereby obtaining an organic substance; and a step of subjecting carbon dioxide generated in at least one of the first and second fermentation steps to methane fermentation to thereby obtain methane, wherein the organic substance obtained in the first fermentation step and the second fermentation step is selected from the group consisting of an alcohol, an organic acid, a fatty acid, a fat and oil, a ketone, a biomass and a saccharide.

5. The method according to claim 4, wherein the first fermentation step is performed so as to cause the gas exhausted from the first fermenter unit to contain hydrogen.

6. The method according to claim 4, which further comprises a step of generating the synthesis gas from the methane.

7. The method according to claim 5, wherein the organic substance is selected from the group consisting of ethanol, acetic acid and butanediol.

* * * * *